United States Patent [19]

Bleier et al.

[11] Patent Number: 4,693,251
[45] Date of Patent: Sep. 15, 1987

[54] CLIP FOR THE OCCLUSION OF AN OVIDUCT OR VAS DEFERENS

[75] Inventors: Waldemar Bleier, Saarlouis; Theodor Lutze, Balgheim; Harald Stallforth, Tuttlingen, all of Fed. Rep. of Germany

[73] Assignee: Aesculap-Werke AG, Tuttlingen, Fed. Rep. of Germany

[21] Appl. No.: 804,160

[22] Filed: Dec. 3, 1985

[30] Foreign Application Priority Data

Dec. 15, 1984 [DE] Fed. Rep. of Germany ....... 3445874

[51] Int. Cl.[4] .............................................. A61B 17/28
[52] U.S. Cl. ..................................... 128/346; 128/325; 128/326
[58] Field of Search ......................... 128/325, 326, 346

[56] References Cited

U.S. PATENT DOCUMENTS 3,608,554 9/1971 McGuinness et al. .............. 128/346
4,545,377 10/1985 Cerwin et al. ...................... 128/346

Primary Examiner—C. Fred Rosenbaum
Assistant Examiner—Sherri E. Vinyard
Attorney, Agent, or Firm—Kenway & Jenney

[57] ABSTRACT

The clip consists of two separate branches, the facing surfaces of which have profiles which allow the pressure effecting occlusion of the oviduct or vas deferens to be generated only in two separate pressure zones while a cavity is formed as nutrition zone between the two pressure zones to relieve the oviduct or vas deferens of pressure and enable its tissue to be nourished. The branches are connected with one another at both ends by detent closure means.

1 Claim, 6 Drawing Figures

CLIP FOR THE OCCLUSION OF AN OVIDUCT OR VAS DEFERENS

The invention relates to a clip for the occlusion of an oviduct or vas deferens (duct) by clamping, consisting of two parts (branches) to be placed transversely to the duct to be clamped and comprising a latching means, these parts exerting pressure on the section of duct (duct section) positioned between them, this pressure being generated by closure of the latching means and causing occlusion of the duct (duct occlusion).

(Due to a lack of any established collective term, the word "duct" and word formations derived therefrom are intended in the following to apply for both an oviduct and a vas deferens).

Clips having the above features serve in human and veterinary medicine as mechanical contraceptive devices which prevent passage of the cells otherwise conducted through the duct by clamping it off.

Known clips consist of two legs or clamping jaws, also designated branches, between which the duct to be clamped is held. For this purpose, the branches are connected with one another on one narrow side by a resilient link means whereas the other narrow side may be closed by interlocking the two legs. A clip of this type is known, for example, from German published application DE-AS No. 27 32 326.

It has become apparent that during use of the known clips the connective tissue of the clamped duct section tends to become so thin and constricted that the clip drops off with the clamped duct section after a certain length of time and control is therefore no longer possible. In the case of an oviduct or tubal occlusion, the clip which has dropped off in this way passes, for example, into the abdominal cavity, in particular the Douglas pouch. The two ends of the tube are still firmly closed with regard to their connective tissue and in this respect the primary effect of the clip is guaranteed. However, the uncontrolled alteration in position or rather the uncontrollable whereabouts of the clip as a foreign body in the organism of the user is undesirable.

The unfavourable behaviour of the clamped duct resulting from use of the known clips is primarily due to the fact that the two branches of the known clips, when closed, have the same distance between them along their entire length. This means that the duct tissue is is squeezed in the clip over its entire width or length and is cut off from the vessels serving to nourish it. The fact that the branches are, at the points of entry and exit of the duct, relatively sharp-edged or have a substantial curvature has proven to have a disadvantageous effect on the clamped duct, the result being that the duct is abruptly crushed at these points.

The object underlying the invention is to design a clip of the type in question such that these disadvantages are no longer incurred. The clip should not squeeze the clamped duct over its entire width and thereby constrict it or cut it off from the vessels serving to nourish it but is intended to prevent a total atrophy due to pressure by maintaining nourishment of the tissue in sections. The mass of the compressed duct tissue is to be reduced and an abrupt crushing of the duct prevented at all positions along the clip.

This object is accomplished by the invention in that the surfaces of the two branches facing the duct section or one another, respectively, have profiles of the type that a pressure effecting duct occlusion may be generated only in two separate regions (pressure zones) of the branches while a cavity (nutrition zone) relieving pressure on the duct and allowing nourishment of its tissue is formed between the two pressure zones, and that the substantially wave-like branch profiles have curvatures which are as slight as possible in each (diagrammatic) sectional plane extending vertically through the duct.

The inventive branch profiles differ fundamentally in their application and purpose from the known branch profiles shown, for example, by the clip of DE-AS No. 27 32 326. In the case of these branch profiles, wherein the clamping surfaces of the branches are equidistant over their entire length, clamping effect and tightness of the duct closure means are intended to be improved by lengthening the effectively clamped duct section beyond the extent determined per se by the width of the clip.

In a particularly advantageous development of the inventive clip, the nutrition zone is continued on both sides of the duct section at right angles thereto and opens outwardly at the two shorter lateral faces or end faces of the clip.

In order to create even more favourable nourishment conditions for the clamped duct section, the clip of an advantageous development of the invention consists of an upper part (closing bridge) having extensions at both ends (locking members), these extensions being provided with catch detents, and a lower part having resilient members (closing arms) at both ends, these arms corresponding to the locking members and also being provided with catch detents, in such a manner that when the closing bridge is pressed into the lower part the catch detents of the locking members and closing arms engage one another and form a self-locking closure of the two parts.

The invention will be explained in the following on the basis of one embodiment and in conjunction with the schematic FIGS. 1 to 6 which are not to scale. In these drawings, FIG. 1 is a view showing the longer side (longitudinal side) of the closed clip;

Figure 1:
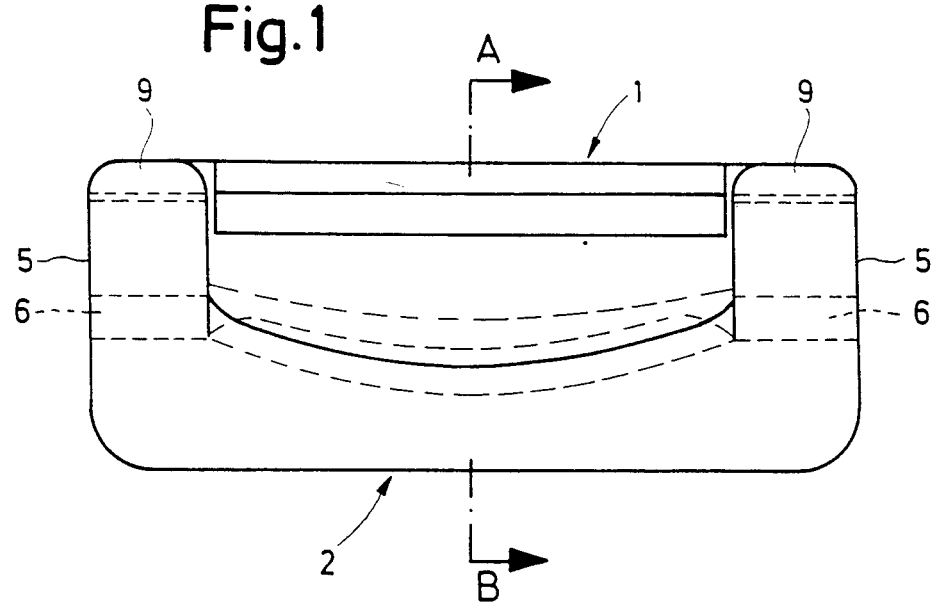
Figure 2:
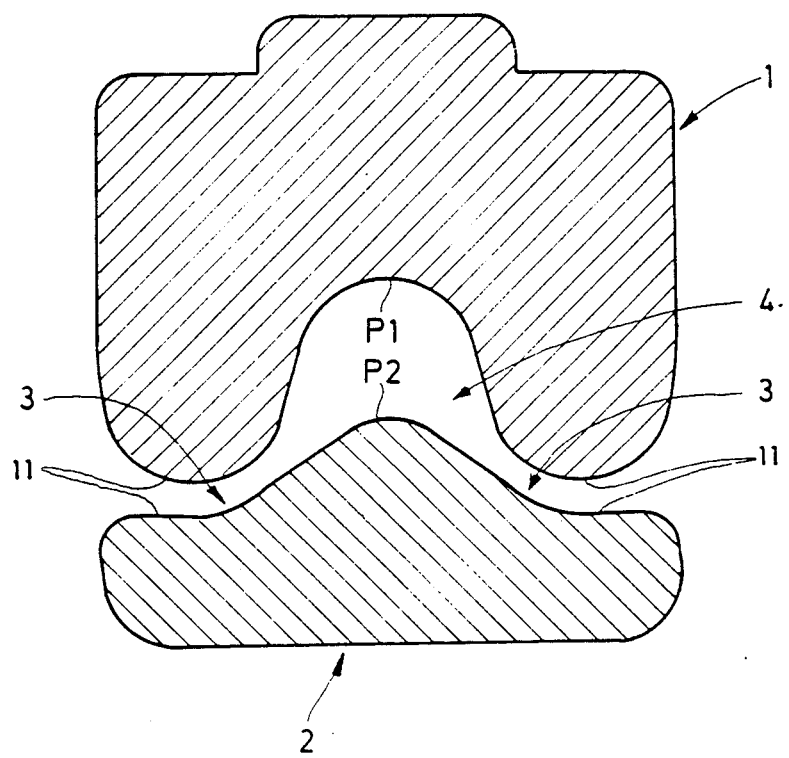
FIG. 2 shows a cross section of the closed clip.
Figure 3:
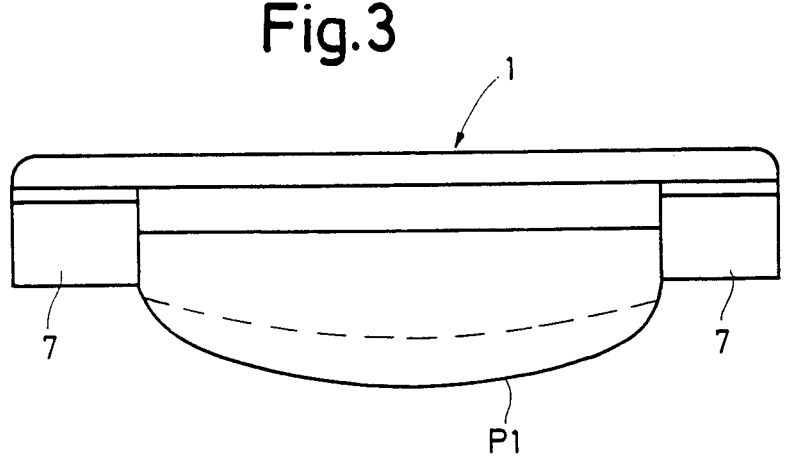
FIG. 3 shows the upper part or closing bridge of the clip.
Figure 4:
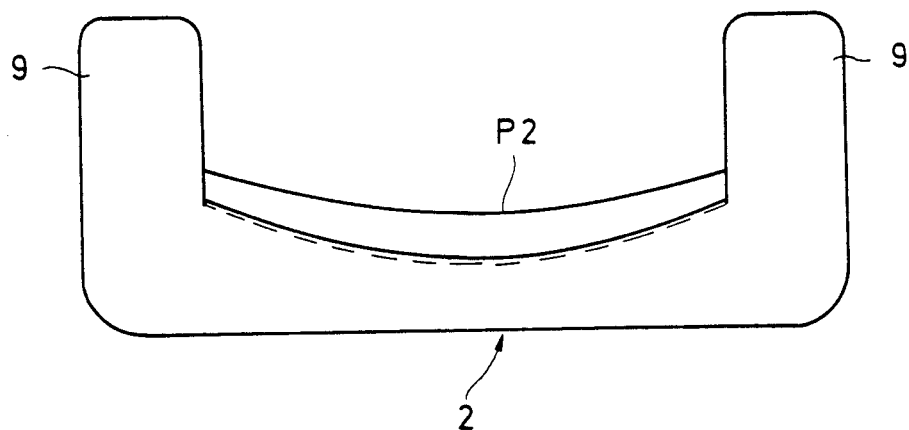
FIG. 4 shows the lower part of the clip.
Figure 5:
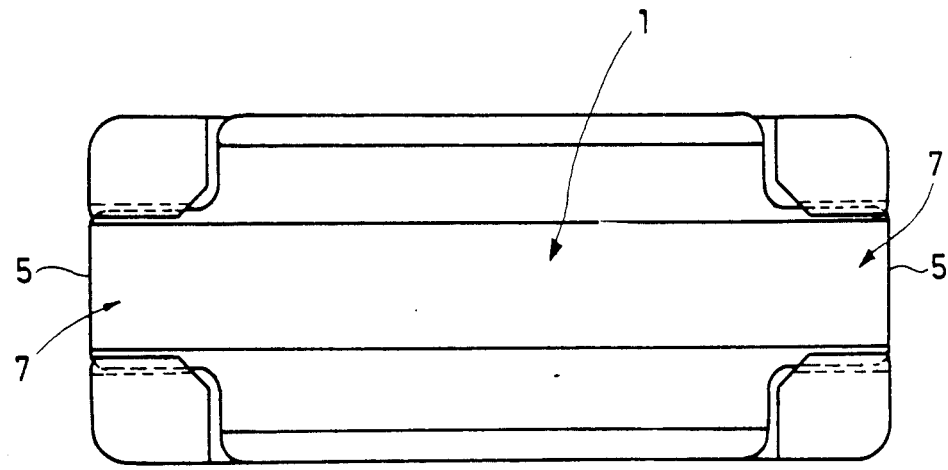
FIG. 5 is a plan view of the closed clip.

The clip shown in FIGS. 1, 2 and 5 in its closed state consists of the upper part or closing bridge 1, which is illustrated in detail in FIG. 3, and the lowerpart 2 shown in detail in FIG. 4. The external dimensions of this closed clip are, in a practical embodiment, approximately 5×5×12 mm.

The branch profile P1 of the closing bridge 1 and the branch profile P2 of the lower part 2 may be considered to be approximately wave-like. As shown by the cross section in FIG. 2, the two branch profiles come close to one another in two separate regions 3 in such a manner that, in these regions, narrow passages are formed which narrow the gap for the duct which traverses the clip in the plane of drawing of FIG. 2 to, in a practical embodiment, about 0.1 to 0.2 mm. The narrow passages 3 therefore form, within the closed clip, two effective pressure zones in which the duct section embraced by the clip is squeezed or clamped to an extent causing duct occlusion.

Outside the pressure zones 3 the duct section is relieved of pressure as a result of the branch profiles P1 and P2 such that nourishment of its tissue is not impaired. For this purpose, the branch profiles P1 and P2 of the assembled clip form a nutrition zone in the form of a cavity 4 between the pressure zones 3. In addition, the closed clip opens outwardly in the shape of a mouth, outside the pressure zones 3, in the regions 11 of its longer side walls. Due to the variations in distance between the facing branch profiles, the compressed duct portions are induced to yield into the nutrition zone 4 and towards the mouth-like openings 11. The mass of the compressed tissue is thereby clearly reduced.

FIG. 2 shows that the branch profiles P1 and P2 have, in the sectional plane A - B extending vertically through the duct, curvatures which are the smallest possible for the predetermined conditions brought about in particular by the external dimensions of the closed clip. This applies not only for the vertically oriented cross-sectional plane but also for all other diagrammatic sectional planes intersecting the duct. In a practical embodiment the greatest curvature, which occurs in this case in the branch profile P1 at the narrow passage 3, is about $1.7 \text{ mm}^{-1}$. It is obvious that abrupt transitions between areas having varying curvatures do not occur in the branch profiles of the invention. An abrupt pinching of the duct is therefore avoided at all points along the clip.

Figure 6:
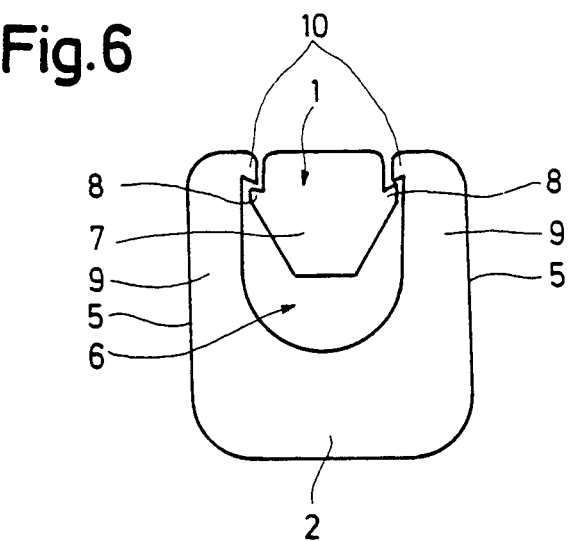
FIG. 6 is a view showing the shorter side or end face of the closed clip.

FIGS. 1 and 6 show that the nutrition zone 4 is continued within the clip towards the shorter side surfaces or end faces 5 of the clip, at which it exits at 6 or rather opens towards the outside. Vessels which extend in a median plane of the duct and serve to nourish the duct tissue, for example the vessles contained in the mesosalpinx membrane of an oviduct, have more or less unhindered access to the duct section within the clip through the openings 6 and 11.

The possibility of nourishing the tissue of the duct section within the clip is additionally improved by the invention in that the inventive clip dispenses with the resilient link means connecting the two branches of the known clip and that the closure between the two branches is designed such that it interferes as little as possible with the nourishing vessels. For this purpose, the upper part or closing bridge 1 has extensions in the form of locking members 7 at both ends which are provided with catch detents 8. The lower part 2 is provided at both ends with closing members in the form of resilient arms 9 which correspond to the locking members 7 and bear catch detents 10. The catch detents on both sides are formed by webs which have an approximately saw-tooth-shaped cross section and extend substantially along the length of the locking members 7 or the width of the closing arms 9. When the closing bridge 1 is pressed into the lower part 2 the catch detents on both sides slide over one another until they engage on one another due to the spring force of the closing arms 9 and form a self-locking closure between the closing bridge 1 and the lower part 2. The closing arms 9 leave space between themselves for outward opening of the nutrition zone 4 at 6.

The material used for the inventive clip may be any natural or artificial material which is biologically compatible and fulfills the mechanical requirements of the construction, in particular metals and plastics already tested for surgical procedures.

We claim:

1. A clip for the occlusion of an oviduct or vas deferens by clamping, consisting of two parts (branches) to be placed transversely to the duct to be clamped and a latching means, said parts exerting pressure on the section of duct (duct section) positioned between them, said pressure being generated by closure of the latching means and causing occlusion of the duct (duct occlusion), wherein the improvement comprises the surfaces of the two branches facing the duct section or one another, respectively, have profiles of the type that a pressure effecting duct occlusion may be generated only in two separate regions of said branches while a cavity relieving pressure on said duct and allowing nourishment of its tissue is formed between said two pressure zones, the substantially wave-like branch profiles having curvatures which are as slight as possible in each sectional plane extending vertically through said duct and having no projecting ridges so as to avoid clamping the tissue under said profiles in a manner that would prevent mourishment of the tissue, said nutrition zone being continued on both sides of the duct section at right angles thereto and opening outwardly at the two shorter lateral faces or end faces of the clip, and said clip comprising an upper part having extensions at both ends, said extensions being provided with catch detents, and a lower part having resilient members at both ends, said arms corresponding to said locking members and also being provided with catch detents, in such a manner that when said closing bridge is pressed into said lower part said catch detents of said locking members and said closing arms engage one another and form a self-locking closure of the two parts.

* * * * *